US010791976B1

(12) United States Patent
Peeters et al.

(10) Patent No.: US 10,791,976 B1
(45) Date of Patent: Oct. 6, 2020

(54) NEEDLE-FREE BLOOD DRAW

(71) Applicant: Verily Life Sciences LLC, Mountain View, CA (US)

(72) Inventors: Eric Peeters, San Jose, CA (US); Peter Howard Smith, Pacifica, CA (US)

(73) Assignee: Verily Life Sciences LLC, Mountain View, CA (US)

( * ) Notice: Subject to any disclaimer, the term of this patent is extended or adjusted under 35 U.S.C. 154(b) by 615 days.

(21) Appl. No.: 15/648,888

(22) Filed: Jul. 13, 2017

Related U.S. Application Data (62) Division of application No. 14/289,362, filed on May 28, 2014, now Pat. No. 9,737,251.

(51) Int. Cl.
*A61B 5/151* (2006.01)
*A61B 5/15* (2006.01)

(52) U.S. Cl.
CPC ........ *A61B 5/15134* (2013.01); *A61B 5/1514* (2013.01); *A61B 5/150022* (2013.01);
(Continued)

(58) Field of Classification Search
CPC ............ A61M 5/14248; A61M 5/2053; A61M 2005/3022; A61M 2037/0007; A61M 5/30; A61B 10/0045; A61B 2010/008; A61B 2017/00747; A61B 2017/00765; A61B 5/14514; A61B 5/15003; A61B 5/150221; A61B 5/150343; A61B 5/150946; A61B 5/15134; A61B 5/1514; A61B 5/150267; A61B 5/15113; A61B 5/15115; A61B 5/15125; A61B 5/150229;
(Continued)

(56) References Cited

U.S. PATENT DOCUMENTS 5,204,253 A   4/1993   Sanford et al.
6,030,399 A   2/2000   Ignotz et al.
(Continued)

OTHER PUBLICATIONS

Bala, et al. "PLGA nanoparticles in drug delivery: the state of the art." Critical Reviews TM in Therapeutic Drug Carrier Systems 21.5 (2004).
(Continued)

*Primary Examiner* — David J. McCrosky
(74) *Attorney, Agent, or Firm* — McDonnell Boehnen Hulbert & Berghoff LLP (57) ABSTRACT

A system for needle-free drawing of blood is disclosed. A hand-portable device can include an evacuated negative-pressure barrel with a membrane sealing an aperture at a distal end, and a housing affixed to a proximal end. An accelerator barrel can be positioned within the negative-pressure barrel and fixed to the housing, with an open proximal end in a chamber in the housing, and an open distal end aligned with the aperture. The chamber can be filled with pressurized gas, and a trigger valve can hydrostatically separate the chamber from the open proximal end of the accelerator barrel. A micro-particle positioned within the accelerator barrel can be accelerated to high speed by an abrupt surge of gas by releasing the trigger valve. The micro-particle can attain enough momentum to pierce the aperture membrane and penetrate adjacent dermal tissue. A resulting micro-emergence of blood can be drawn into the negative pressure barrel.

12 Claims, 5 Drawing Sheets

(52) U.S. Cl.
CPC .... *A61B 5/150099* (2013.01); *A61B 5/15125* (2013.01); *A61B 5/150343* (2013.01); *A61B 5/15115* (2013.01); *A61B 5/150175* (2013.01)

(58) Field of Classification Search
CPC ........ A61B 5/150236; A61B 5/150022; A61B 5/150099; A61B 5/157; A61B 5/15123
See application file for complete search history.

(56) References Cited

U.S. PATENT DOCUMENTS

| | | |
|---|---|---|
| 6,207,400 B1 | 3/2001 | Kwon |
| 6,210,359 B1 | 4/2001 | Patel et al. |
| 6,324,779 B1 | 12/2001 | Tippmann, Jr. |
| 6,706,032 B2 | 3/2004 | Weaver et al. |
| 7,320,677 B2 | 1/2008 | Brouillette |
| 7,892,836 B2 | 2/2011 | Groisman et al. |
| 7,942,846 B2 | 5/2011 | Bellhouse et al. |
| 2002/0045912 A1* | 4/2002 | Ignotz ................ A61B 17/3203 606/167 |
| 2004/0065310 A1 | 4/2004 | Masse |
| 2005/0176084 A1 | 8/2005 | Burkoth |
| 2005/0177098 A1 | 8/2005 | Lin et al. |
| 2006/0129065 A1 | 6/2006 | Matsumoto et al. |
| 2007/0191758 A1 | 8/2007 | Hunter et al. |
| 2008/0206870 A1* | 8/2008 | Groisman .............. C12M 35/00 435/440 |
| 2010/0307472 A1 | 12/2010 | Witzigreuter |
| 2012/0123297 A1 | 5/2012 | Brancazio |
| 2016/0089496 A1 | 3/2016 | Brouillette et al. |

OTHER PUBLICATIONS

Kawai, et al. "Single microparticle launching method . . . " Review of Scientific Instruments 81.11 (201 0): 115105.

* cited by examiner

NEEDLE-FREE BLOOD DRAW

CROSS-REFERENCE TO RELATED APPLICATIONS

The present application is a divisional of, and claims priority to, U.S. application Ser. No. 14/289,362, filed on May 28, 2014, which is hereby incorporated in its entirety herein by reference.

BACKGROUND

Unless otherwise indicated herein, the materials described in this section are not prior art to the claims in this application and are not admitted to be prior art by inclusion in this section.

A number of scientific methods have been developed in the medical field to evaluate physiological conditions of a person by detecting and/or measuring one or more analytes in a person's blood or other bodily fluids or tissues. The one or more analytes could be any analytes that, when present in or absent from the blood, or present at a particular concentration or range of concentrations, may be indicative of a medical condition or health state of the person. The one or more analytes could include enzymes, reagents, hormones, proteins, cells or other molecules, such as carbohydrates, e.g., glucose.

In a typical scenario, a person's blood is drawn and either sent to a lab or input into a handheld testing device, such as a glucose meter, where one or more tests are performed to measure various analyte levels and parameters in the blood. The frequency and regularity of such blood tests can depend on the type of test and the nature of the condition or conditions being monitored. For example, testing for blood glucose concentration for a person with diabetes may be performed relatively frequently.

SUMMARY

In one aspect, a hand-portable device includes: an evacuated negative-pressure barrel with an aperture membrane sealing an aperture at a distal end of the evacuated negative-pressure barrel, and a housing affixed to, and sealing, a proximal end of the evacuated negative-pressure barrel; an accelerator barrel positioned lengthwise within the evacuated negative-pressure barrel with an open proximal end fixed to the housing and opening into a chamber within the housing, and having an open distal end proximate to, and aligned with, the aperture; a high-pressure gas source configured for filling the chamber with pressurized gas; a trigger valve situated between, and forming a hydrostatic boundary between, the chamber and the open proximal end of the accelerator barrel; a micro-particle positioned within the accelerator barrel at a launch point proximate to the trigger valve; and a trigger-valve release actuator configured for abruptly opening of the trigger valve to abruptly release the pressurized gas from the chamber and into the open proximal end of the accelerator barrel, wherein, the abruptly released pressurized gas is configured to accelerate the micro-particle from the launch point to the open distal end of the accelerator barrel and through the aperture with sufficient momentum to pierce through the aperture membrane and penetrate a sufficient depth of dermal tissue proximate to the distal end of the evacuated negative-pressure barrel to induce a micro-emergence of blood at the dermal tissue surface, and wherein, residual negative pressure within the evacuated negative-pressure barrel is configured to draw at least a portion of blood from the micro-emergence into the evacuated negative-pressure barrel through the pierced aperture membrane.

In another aspect, a hand-portable device includes: an outer barrel with an aperture at a distal end, and a housing affixed to a proximal end; a hydrophilic absorptive wick in the outer barrel, unobstructively surrounding at least a portion of the aperture; an inner barrel positioned lengthwise within the outer barrel with an open proximal end fixed to the housing and opening into a chamber within the housing, and having an open distal end proximate to, and aligned with, the aperture; a high-pressure gas source configured for filling the chamber with pressurized gas; a trigger valve situated between, and forming a hydrostatic boundary between, the chamber and the open proximal end of the inner barrel; a micro-particle positioned within the inner barrel at a launch point proximate to the trigger valve; and a trigger-valve release actuator configured for abruptly opening of the trigger valve to abruptly release the pressurized gas from the chamber and into the open proximal end of the inner barrel, wherein, the abruptly released pressurized gas is configured to accelerate the micro-particle from the launch point to the open distal end of the inner barrel and through the aperture with sufficient momentum to penetrate a sufficient depth of dermal tissue proximate to the distal end of the outer barrel to induce a micro-emergence of blood at the dermal tissue surface, and wherein, the hydrophilic absorptive wick is configured to draw at least a portion of blood from the micro-emergence into outer barrel through the aperture by capillary action.

In still another aspect, a hand-portable device includes: a negative-pressure barrel having an aperture opening at a distal end and a housing affixed to a proximal end; an accelerator barrel positioned lengthwise within the negative-pressure barrel with an open proximal end fixed to the housing and opening into a chamber within the housing, and having an open distal end proximate to, and aligned with, the aperture; a high-pressure gas source configured for filling the chamber with pressurized gas; a trigger valve situated between the chamber and the open proximal end of the accelerator barrel, the trigger valve having a closed operational state in which the trigger valve is closed so as to form a hydrostatic boundary between the chamber and the open proximal end of the accelerator barrel, and an open operational state in which the trigger valve is opened so as to remove the hydrostatic boundary; an arming actuator configured for setting the hand-portable device in an armed operational state in which (i) the trigger valve is set in the closed operational state, (ii) the chamber is filled with pressurized gas, (iii) a micro-particle is positioned within the accelerator barrel at a launch point proximate to the trigger valve, (iv) a negative-pressure vacuum is created within the negative-pressure barrel and within the accelerator barrel between the open distal end and the closed trigger valve, and (v) an aperture membrane is configured to seal the aperture and maintain the negative-pressure vacuum; and a trigger-valve release actuator configured for causing the trigger valve to abruptly transition from the closed operational state to the open operational state, thereby abruptly releasing the pressurized gas from the chamber into the open proximal end of the accelerator barrel, wherein, the abruptly released pressurized gas is configured to accelerate the micro-particle from the launch point to the open distal end of the accelerator barrel and through the aperture with sufficient momentum to pierce through the aperture membrane and penetrate a sufficient depth of dermal tissue proximate to the distal end of the negative-pressure barrel to induce a micro-emergence of blood at the dermal tissue surface, and wherein, the negative-pressure vacuum within the negative-pressure barrel is configured to draw at least a portion of blood from the micro-emergence into the negative-pressure barrel through the pierced aperture membrane.

In yet another aspect, a method involves: evacuating a negative-pressure barrel of a hand-portable device, the evacuated negative-pressure barrel having an aperture membrane sealing an aperture at a distal end of the negative-pressure barrel, and a housing affixed to, and sealing, a proximal end of the negative-pressure barrel, wherein the negative-pressure barrel contains an accelerator barrel positioned lengthwise within the negative-pressure barrel with an open proximal end fixed to the housing and opening into a chamber within the housing, and having an open distal end proximate to, and aligned with, the aperture; arming a trigger valve situated between the chamber and the open proximal end of the accelerator barrel, the armed trigger valve forming a hydrostatic boundary between chamber and the open proximal end of the accelerator barrel; configuring a micro-particle within the accelerator barrel at a launch point proximate to the trigger valve; by abruptly releasing the armed trigger valve, abruptly releasing pressurized gas from the chamber and into the open proximal end of the accelerator, wherein, the abruptly released pressurized gas is configured to accelerate the micro-particle from the launch point to the open distal end of the accelerator barrel and through the aperture with sufficient momentum to pierce through the aperture membrane and penetrate a sufficient depth of dermal tissue proximate to the distal end of the negative-pressure barrel to induce a micro-emergence of blood at the dermal tissue surface; and drawing at least a portion of blood from the micro-emergence into the evacuated negative-pressure barrel through the pierced aperture.

In yet one further aspect, a method involves: configuring a micro-particle at a launch point at a proximal end of an accelerator barrel of a hand-portable hyperspeed micro-particle accelerator device, wherein the accelerator barrel is positioned lengthwise within an outer barrel of the hand-portable hyperspeed micro-particle accelerator device and has an open distal end proximate to, and aligned with, an aperture at a distal end of the outer barrel; arming the hand-portable hyperspeed micro-particle accelerator device for hyperspeed acceleration of the micro-particle; and triggering the armed hand-portable hyperspeed micro-particle accelerator device to cause the micro-particle to accelerate from the launch point to the open distal end of the accelerator barrel and through the aperture with sufficient momentum to pierce dermal tissue proximate to the distal end of the outer barrel with no larger than a dermal-pore-sized surface puncture.

These as well as other aspects, advantages, and alternatives, will become apparent to those of ordinary skill in the art by reading the following detailed description, with reference where appropriate to the accompanying drawings.

DETAILED DESCRIPTION

In the following detailed description, reference is made to the accompanying figures, which form a part hereof. In the figures, similar symbols typically identify similar components, unless context dictates otherwise. The illustrative embodiments described in the detailed description, figures, and claims are not meant to be limiting. Other embodiments may be utilized, and other changes may be made, without departing from the scope of the subject matter presented herein. It will be readily understood that the aspects of the present disclosure, as generally described herein, and illustrated in the figures, can be arranged, substituted, combined, separated, and designed in a wide variety of different configurations, all of which are explicitly contemplated herein.

Further, while embodiments disclosed herein make reference to use on or in conjunction with a living human body, it is contemplated that the disclosed methods, systems and devices may be used in any environment where needle-free drawing of blood, and/or needle-free, sub-dermal delivery of diagnostic and/or therapeutic substance, is desired. The environment may be any living or non-living body or a portion thereof, a fluid conduit, a fluid reservoir, etc.

1. Overview

Some types of medical testing involve analysis of very small blood samples from a person (e.g., a medical patient). For example, monitoring of a blood-sugar level may be able to be achieved with just a tiny droplet of blood (e.g., a fraction of a milliliter). Common techniques of medical blood extraction typically entail piercing the dermal tissue (skin) with a small needle or lancet (a "piercing element"), and collecting blood from the puncture point. In the case of a hollow needle, collection may be made below the skin, in a vein or capillary for example. For a lancet or non-hollow needle, collection may be made at the skin surface as the blood emerges.

Generally, the smaller the puncture, the smaller the degree of discomfort that may accompany a blood draw. Consequently, very small diameter needles or lancets may be considered advantageous for purposes at least of comfort of the patient. In practice, small piercing elements can be integrated in small, hand-portable implements that can be used by a healthcare practitioner, or even the patient, to collect a small sample of the patient's blood and provide it to a lab for testing.

While decreasing the size (e.g., diameter) of a piercing element can help decrease discomfort, it can also reduce the tensile strength of the piercing element so that it can no longer pierce dermal tissue, but bends or breaks when applied instead. In particular, the size limit at which the tensile strength of a piercing element is no longer sufficient to reliably pierce dermal tissue may still be larger than that at which the discomfort associated with piercing dermal tissue vanishes or becomes imperceptible. Accordingly, example embodiments disclosed herein provide an example device and technique for medical extraction of blood that can imperceptibly pierce dermal tissue without a piercing element.

In one example, a small, hand-portable device can include a pneumatic particle accelerator for imparting a micro-particle with a sufficient momentum to cause it to pierce dermal tissue deep enough to induce a micro-emergence of blood at the surface of the dermal tissue. In accordance with example embodiments, the micro-particle can be small enough, and can be accelerated fast enough and to a high enough kinetic energy, to imperceptibly pierce the dermal tissue. The hand-portable device can include a vacuum barrel that, when positioned at or above the dermal tissue surface at the entry point of the micro-particle, can draw at least a portion of blood from the micro-emergence. Also in accordance with example embodiments, the micro-emergence of blood can be of sufficient volume for a variety of medical blood analysis tests. In one example, the hand-portable device could be hand-held, and comparable in size and form factor to a pencil or conventional hypodermic needle-carrying barrel. In another example, the hand-portable device could be wearable, for instance attached to a wristband, and comparable in size and form factor to a small electronic device, such as USB flash memory drive. Other sizes and form factors are possible as well.

In accordance with example embodiments, an example small, hand-portable device can include an outer barrel having an aperture at a distal end and a housing at a proximal end. The device can also include an inner barrel positioned lengthwise within the outer barrel, with an open proximal end attached to the housing and with an open distal end proximate to, and aligned with, the aperture. The outer and inner barrels can be co-aligned along a straight or curved lengthwise direction. The housing can include a chamber where the open proximal end of inner barrel attaches to the housing, and into which the open proximal end of the inner barrel opens. The chamber can also include or contain a pressurized gas source is located. The chamber and the open proximal end of the inner barrel can be separated by a trigger valve, which in a closed operational state forms a hydrostatic boundary between the chamber and the open proximal end of the inner barrel.

In further accordance with example embodiments, the trigger valve can include a trigger-valve release actuator, capable of abruptly opening the closed trigger valve instantaneously (i.e., nearly instantaneously). When the trigger valve is in an open operational state, the chamber and the open proximal end of the inner barrel are hydro-dynamically connected to one another, such that gas can flow from one to the other according to any pressure differential between them.

In further accordance with example embodiments, a micro-particle can be positioned at a launch point within the inner barrel at the proximal end of the inner barrel, near the trigger valve. The outer barrel can be evacuated to negative internal pressure (with respect to air pressure outside the outer barrel), and sealed with a membrane covering the aperture at the distal end and with the closed trigger valve between the chamber and the open proximal end of the inner barrel. In this "armed operational state," a constant negative pressure can be maintained throughout the outer barrel and the inner barrel, up to the closed trigger valve. That is, the negative pressure corresponds to a vacuum pervading the outer barrel and the inner barrel, up to the closed trigger valve.

In an example embodiment, the pressurized gas source in the chamber can be configured to generate high pressure gas, for example by a chemical reaction or an electro-chemical reaction. Such a reaction can be made to occur extremely rapidly, so as to be nearly instantaneous. Alternatively, the pressurized gas source can be a small container (e.g., a cartridge) of pre-pressurized gas configured to fit within the chamber. The pressurized gas source can be considered to be in a "ready state" when it is capable of instantly (or nearly instantly) releasing its pressurized gas through the closed trigger valve and into the open proximal end of the inner barrel. For example, in the ready state, the chamber can be directly filled with the pressurized gas, either from a reaction or a pre-pressurized cartridge, and thereafter maintained at pressure and ready for release by the closed trigger valve. Alternatively, a distinct cartridge of pre-pressurized gas can be located within the chamber, with an outlet connected to the closed trigger valve. Other arrangements for providing a ready state of the pressurized gas source are possible as well.

In further accordance with example embodiments, the armed operational state of the device can also include the pressurized gas source being in its ready state. Thus, in the armed operational state, a vacuum pervades the outer barrel and the inner barrel up to the closed trigger valve, a micro-particle is situated in the inner barrel at the launch point, and the pressurize gas source is ready to deliver a surge of high pressure gas through the closed trigger valve and directed through the inner barrel toward the aperture, with the micro-particle in the direct path of the high-pressure surge. For descriptive purposes, the proximal end of the device (e.g., proximal end of the housing) can be referred to as the "upstream" end or direction, and the distal end of the device (e.g., distal end of the outer barrel) can be referred to as the "downstream" end or direction. This terminology signifies the direction of the flow of gas and of the micro-particle motion, from upstream to downstream, when pressure is released by abrupt opening of the close trigger valve.

The device can be used to collect a sample of blood in accordance with example embodiments as follows. With the device in the armed operational state, the aperture at the distal end of the outer barrel can be positioned at the surface of the dermal tissue. More particularly, the device can be oriented such that the upstream-to-downstream direction is approximately perpendicular to the surface of the dermal tissue, with the aperture resting against or just above the surface. While being held in this position and orientation, the trigger-valve release actuator can be actuated, resulting in an instantaneous (or nearly instantaneous) release of pressurized gas from the chamber into the open proximal end of the inner barrel. This abrupt release of high pressure gas into the inner barrel can thus manifest as a sudden surge of pressure entering the open proximal end of the inner barrel, and rapidly moving in the downstream direction. When this surge hits the micro-particle at the launch point, it imparts a very large impulse that can accelerate the micro-particle rapidly downstream in the inner barrel and out the opening at the distal end of the inner barrel, where the micro-particle then speeds toward and through the aperture. Even subsequent to the initial impulse, the high-velocity flow of gas downstream can continue to accelerate the micro-particle as it moves downstream through the inner barrel. It can be shown that the hydrodynamics of this process can accelerate the micro-particle to supersonic speed, especially if the inner barrel incorporates a shape—such as a nozzle—that conditions the flow, as described below. In particular, sufficient momentum can be imparted to the micro-particle by the time it emerges from the open distal end of the inner barrel so that it breaks through the membrane (after traveling through the aperture), pierces the adjacent dermal tissue, and travels to depth several times larger than its own size before coming to a stop. The high speed acquired by the micro-particle in this process is referred to herein as "hyperspeed," and can approach or exceed supersonic levels.

In accordance with example embodiments, the micro-particle can be made small enough so that the resulting cross-sectional size of the puncture to the dermal tissue (e.g., approximate cross-sectional size of the micro-particle) is below a size that would be generally perceptible. At the same time, the rapidity with which the piercing takes place further reduces any physical sensation the might be accompanied with the piercing action. However, the micro-particle can nevertheless penetrate to a depth that results in a momentary "micro-emergence" of blood at the site of the piercing. In further accordance with example embodiments, the process of the micro-particle breaking through the membrane, piercing the dermal tissue, and inducing the micro-emergence can happen sufficiently rapidly that a substantial residual negative pressure remains in the outer barrel when the micro-emergence occurs. This negative pressure, in turn, can then tend to draw up at least a portion of the blood in the micro-emergence, thereby collecting blood from an imperceptible piercing of the dermal tissue—a piercing that is accomplished without using a piercing element, such as a needle or lancet. By way of example, a micro-emergence of blood could yield as little as 0.01 milliliters, roughly comparable to a single mosquito bite. This is small enough to be imperceptible, but large enough to carry out a wide variety of medical tests and/or monitoring.

In accordance with example embodiments, the micro-particle can have a spherical, ellipsoidal, or cylindrical shape (e.g., dart-shaped), and a characteristic size (e.g., diameter) in range of 10 μm (microns)-250 μm. The micro-particle can be metallic (e.g., iron or gold) or biodegradable (e.g., salt, sugar, or polylactic-co-glycolic acid (PLGA)). The micro-particle can also be composed of multiple, smaller particles, or an agglomerate of smaller particles. For example, the micro-particle could be made of nano-sized gold particles bound together with biodegradable glue. In general, the higher the density of the micro-particle, the deeper the penetration of the dermal tissue. Other forms and compositions of micro-particles are possible as well. For example, the micro-particle could be composed of a liquid, such as water, and take the form of a small droplet.

Also in accordance with example embodiments, the micro-particle can penetrate the dermal tissue to a depth in a range of 0.25 mm-2 mm. At shallower depths, blood draw may tend to be superficial, while deep depths may result intravenous blood draws.

In further accordance with example embodiments, the micro-particle can include medication, such that penetration of the dermal tissue serves to deliver the medication into the dermal tissue. At shallower depths, delivery can be subcutaneous; at deeper penetration, delivery can be intravenous.

In accordance with example embodiments, the membrane used to seal the aperture can be a thin foil. Alternatively, an open aperture can be placed directly against the dermal tissue before evacuating the outer barrel. In this configuration the dermal tissue itself can serve as the membrane.

In one example, the hand-portable device can be configured as a single-use device. In another example, the hand-portable device can be configured as a multiple-use device. By way of example, a single-use device could come pre-configured with a membrane seal on the aperture, and in the armed operational state. Alternatively, a single-use device could come pre-configured with the membrane seal, but requiring an arming action to evacuate the interior volume and arm the trigger valve. Other configurations of single-use devices are possible as well.

Also by way of example, a multiple-use device could rely on positioning the aperture against the dermal tissue to form the seal at the aperture, and further require a subsequent arming action to evacuate the interior volume and arm the trigger valve to prepare the device for each use. A multiple-use device could also include a pressurized gas source capable of providing multiple allocations of pressurized gas, for example using a metering valve, such that each use of the device gets a new allocation for a new ready state. In addition, a multiple-use device could include multiple micro-particles that can be loaded into the inner barrel, for example by the arming action, also for preparing the device for each use. Further, a multiple-use device could include a removable/replaceable collection reservoir for accommodating each collection of a drawn blood sample.

Other configurations of multiple-use devices are possible as well. For example, a multiple-use device could include a reusable housing with a pressurized gas source and a trigger-release actuator, and multiple, single-use components each including the outer and inner barrels with a micro-particle pre-positioned at the launch point. A new (i.e., replacement) single-use component could be installed in the reusable housing prior to use. Once installed, the hand-portable device could be used for a needle-free blood draw as described, and the single use component, containing the drawn blood, could be removed for delivery to a lab or a local analysis apparatus.

The inner barrel can be described as a hollow cylinder, the interior of which forms a cylindrical channel through which the micro-particle travels, and through which the pressure surge flows from upstream to downstream as it accelerates the micro-particle. In one example, the cylindrical channel interior of the inner barrel can have circular cross-section of constant radius along the entire length of the inner barrel, from its proximal end to its distal end.

In another example, the cylindrical channel interior of the inner barrel can have circular cross-section of constant radius along most the length of the inner barrel, except for a short segment between the open proximal end of the inner barrel and the launch point, over which the cross-sectional shape of the cylindrical channel is altered so as to form a nozzle. For example, within the short nozzle segment, the inner cylindrical channel can have a portion formed to be narrower than the rest of the length of the inner barrel. The hydrodynamic property of such a nozzle is such that the pressure surge entering the nozzle from the upstream side emerges from the downstream side as a supersonic flow. Then by initially positioning the micro-particle at the launch point on the downstream side of the nozzle, the micro-particle can receive its initial impulse, and be further accelerated by, a supersonic flow of gas.

In accordance with example embodiments, the cross-sectional diameter of the micro-particle can be configured to be only slightly smaller than the inner diameter or the inner barrel—i.e., the diameter of the major length of the inner cylindrical channel (excluding the narrowed diameter of the nozzle segment, if any). Thus, the micro-particle can be a close fit, or a "flush" fit, in cross-sectional size to the diameter of the cylindrical channel, but still have sufficient clearance to travel freely from upstream to downstream under the power of the pressure surge. This configuration can help ensure that a majority of the pressure surge stays behind the micro-particle as it is accelerated, and minimizes portions of the pressure surge that might tend to leak past the micro-particle by way of the small clearance between the micro-particle and the circular wall of cylindrical channel. In addition, the vacuum that pervades the interior of the device in the armed operational state, and while the micro-particle is accelerating but has not yet exited the aperture, helps minimize any drag or backpressure on the micro-particle by minimizing the mass of gas that can be swept up in front of the micro-particle as in moves downstream.

Figure 2:
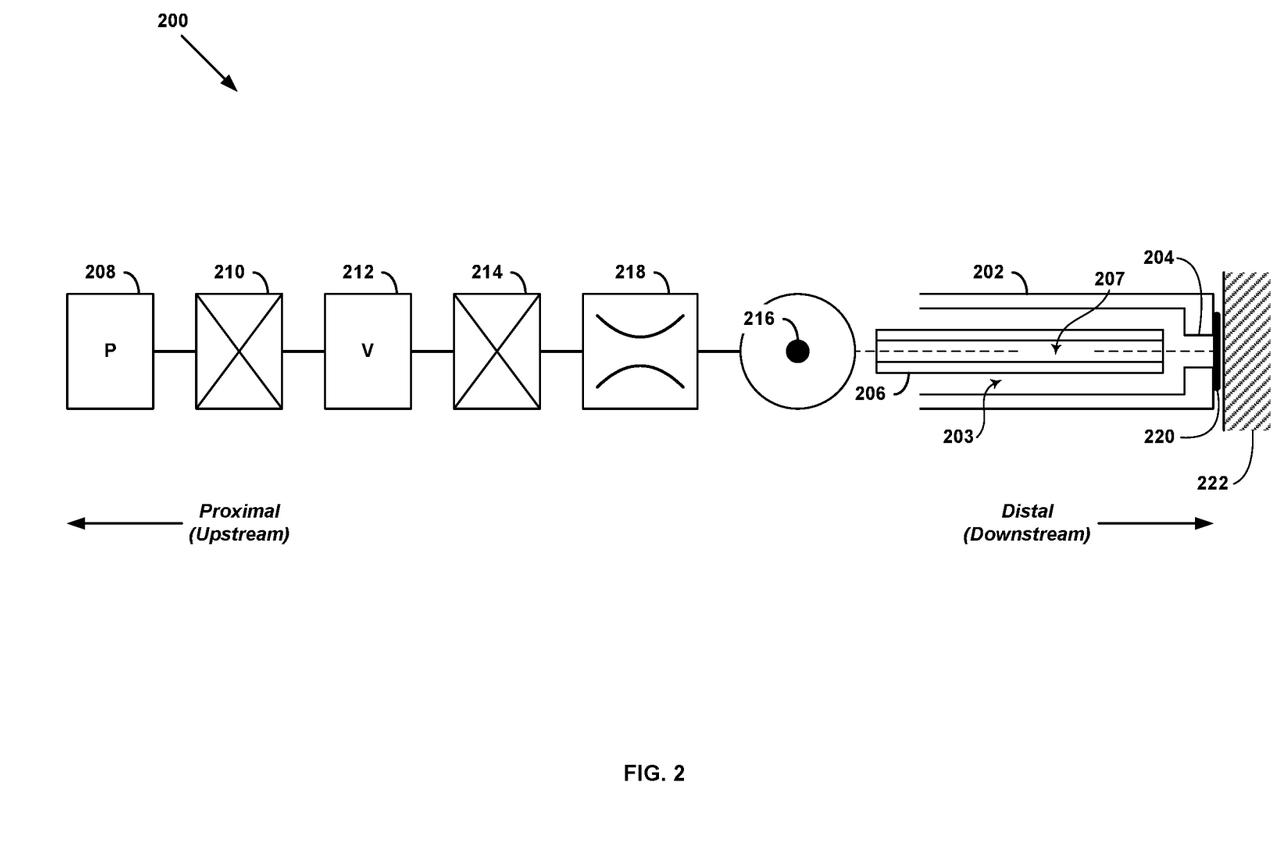
FIG. 2 is a block diagram of a hand-portable device for needle-free blood draw, according to an example embodiment.

It should be understood that the above embodiments, and other embodiments described herein, are provided for explanatory purposes, and are not intended to be limiting.

Further, the term "medical condition" as used herein should be understood broadly to include any disease, illness, disorder, injury, condition or impairment—e.g., physiologic, psychological, cardiac, vascular, orthopedic, visual, speech, or hearing—or any situation requiring medical attention and/or monitoring.

2. Example Hand-Portable Device

FIG. 1A shows one form of an example hand-portable device 100 in an example use context for needle-free blood draw from a hand 102, which is presumed for purposes of illustration to represent a person (e.g., a medical patient). The hand-portable device 100 as shown could be hand-held, such that it is held in place and operated by an operator's hand (not shown in FIG. 1A). In the example use context illustrated in FIG. 1A, the hand-portable device is positioned against the index finger of the hand 102. Such an application might be used to draw a small amount of blood, for example, for a glucose test.

The illustration of FIG. 1A is intended to show an example representative size and form factor for the hand-portable device described herein by way of example, although not necessarily to show specific details of the hand-portable device. As such, the hand-portable device 100 can be taken as an example in terms of size relative to a person's hand (e.g., hand 102). The apparent cylindrical shape of the hand-portable device 100 can also be taken as an example representative shape. It will be appreciated that specific implementations of a hand-portable device for needle-free blood draw in accordance with example embodiments described herein could differ in form and size from the hand-portable device 100 shown in FIG. 1A. Nevertheless, the hand-portable device 100 can be taken as generalized representation for characterizing the size and form factor of example embodiments, while not necessarily ruling out other sizes and/or form factors.

FIG. 1B shows an alternative embodiment of the form of an example hand-portable device 104 in an example use context for needle-free blood draw from a hand 106, again presumed for purposes of illustration to represent a person (e.g., a medical patient). The hand-portable device 104 as shown could be wearable device, held in place by a wrist-band, for example (as shown); operation could be manual or automatic with such a wearable configuration. In the example use context illustrated in FIG. 1B, the hand-portable device is positioned against the wrist of the hand 106. Again, application of the device might be used for drawing a small amount of blood, for example, for a glucose test.

The position and orientation of the hand-portable device 100 and or 104, in particular in contact with the index finger or wrist, can also be taken as representative of how example embodiments can be applied in practice. Namely, one end of the hand-portable device 100 or 104 can be held against, or just above, the skin of the finger or wrist. It is contemplated that an example hand-portable device could be applied at other parts or locations of a person for needle-free blood draw (or for delivery of medications or therapeutic monitoring substances, for example). For purposes of discussion, the term "dermal tissue" will be used herein to refer to the skin of a person (e.g., a medical patient) whose blood is (or will be) drawn using an example hand-portable device for needle-free blood draw. The term "dermal tissue" will similarly apply to embodiments in which needle-free piercing is used for sub-dermal delivery of medications or therapeutic monitoring substances. Furthermore, unless stated otherwise, the term "dermal tissue" will not necessarily specify or require a particular part of, or location on, a person.

FIG. 2 is a functional block diagram of a hand-portable device 200 for needle-free blood draw in accordance with example embodiments. The example hand-portable device 200 can be generally described has having an elongated shape along what shall be referred to as a longitudinal dimension (horizontal in the illustration of FIG. 2). For purposes of discussion, two opposite directions along the longitudinal dimension of the hand-portable device 200 can be defined. Namely, a "proximal" direction and an opposite "distal" direction. The hand-portable device 200 can correspondingly be described as having a proximal end and a distal end. Various components of the hand-portable device 200 can similarly be described as having proximal and distal end or sides. Such descriptions serve to establish the orientation of the components with respect to the proximal and distal directions, and with respect to each other. In the illustration of FIG. 2, the proximal direction is depicted to the left, and the distal direction is depicted to the right. For reasons described below, the proximal direction is also referred to herein as the "upstream" direction, and the distal direction is also referred to herein as the "downstream" direction.

In accordance with example embodiments, the hand-portable device 200 includes an outer barrel 202 with an interior volume 203, and having an aperture 204 at its distal end. As shown in the FIG. 2, an inner barrel 206 is positioned longitudinally within, and co-aligned with, the outer barrel 202. The inner barrel 206 has an interior channel 207 running its length and is open at both its proximal and distal ends, such that the inner barrel 206 can be described as forming a tube. The open distal end of the inner barrel 206 is proximate to, and aligned with, the aperture 204. The outer barrel 202 is also referred to below as a "negative pressure" barrel, and the inner barrel 206 is also referred to below as an "acceleration" barrel.

In further accordance with example embodiments, the distal end of the outer barrel 202 has a membrane 220 that covers and seals the aperture 204. In an operational position in which the hand-portable device is ready (or made ready) for use (e.g., ready to draw blood), the distal end of the outer barrel 202 is placed against (or possibly just very close to) dermal tissue 222.

The hand-portable device 200 further includes a high-pressure gas source 208 (labeled "P") near its proximal end. The high-pressure gas source 208 is connected to a chamber volume 212 (labeled "V") by way of an intervening metering valve 210. The chamber volume 212 is, in turn, connected to a flow conditioner 218 by way of an intervening trigger valve 214. The flow conditioner 218 feeds into the open proximal end of the inner barrel 206. A micro-particle 216 is initially positioned at a launch point within the interior channel 207 of the inner barrel 206, near its proximal end, and distal of the flow conditioner 218. Note that the neither the sizes of the components, nor their relatives sizes, are necessarily shown to scale in FIG. 2.

Example operation of the hand-portable device 200 can be described in accordance with example embodiments as follows. The trigger valve 214 can be configured in a closed state and an open state, and can include a release actuator (not necessarily shown in FIG. 2) for causing the trigger valve to abruptly transition from its closed to its open state—i.e., to abruptly open. With the trigger valve in its closed state, such that it forms a hydrostatic boundary between the chamber volume 212 and the open proximal end of the inner barrel 206, the chamber volume 212 is filled with pressurized gas from the high-pressure gas source 208. Note that the open proximal end of the inner barrel 206 can actually correspond to the proximal end of the flow conditioner 218. The metering valve 210 can be used to help ensure that a measured amount of gas from the high-pressure gas source 208 is allocated for this purpose. The interior volume 203 of the outer barrel can be evacuated to form a vacuum within the interior volume 203 and the interior channel 207 up to the trigger valve 214. The closed trigger valve 214 and the membrane 220 sealing the aperture 204 can then serve to maintain the vacuum. In this configuration, the hand-portable device 200 can be said to be "armed" or in an "armed state."

Figure 1A:
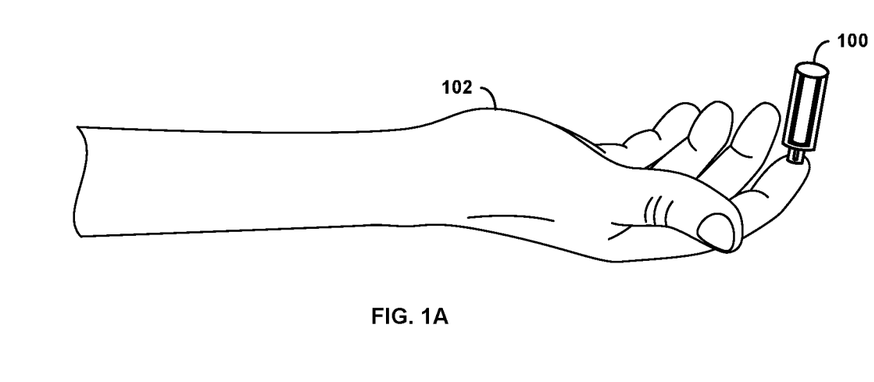
FIG. 1A is an example hand-portable device for needle-free blood draw displayed in an example use context, in accordance to an example embodiment.
Figure 1B:
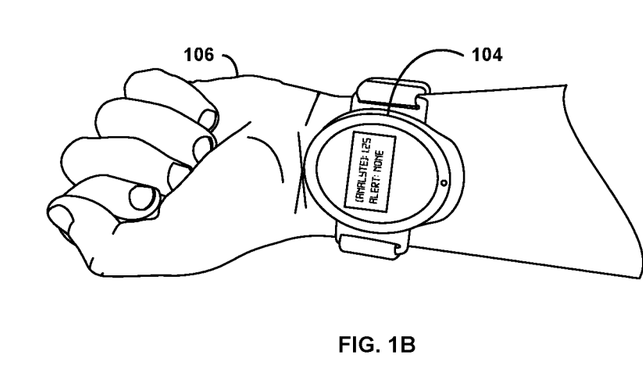
FIG. 1B is an example hand-portable device for needle-free blood draw displayed in an example use context, in accordance to an alternative example embodiment.

In the armed state, the hand-portable device 200 can be positioned and held with its distal end against the dermal tissue 222, as shown, and with its longitudinal direction approximately perpendicular to the dermal tissue surface (as illustrated, for example, in FIG. 1). While being held in this position, the release actuator of the trigger valve 214 can be actuated to cause the trigger valve 214 to abruptly open, thereby abruptly releasing a surge of pressurized gas from the chamber volume 212 into the open proximal end of the inner barrel 206 by way of the flow conditioner 218. As discussed below, the flow conditioner 218 can cause the pressure surge entering its proximal end to exit the distal end of the flow conditioner 218 as an enhanced flow, possibly even a supersonic flow. This enhanced flow, traveling in the distal direction, then hits the micro-particle 216 at the launch point, imparting a large and sudden impulse, and causing the micro-particle to rapidly accelerate through the interior channel 207 the open distal end of the inner barrel 206.

As the micro-particle 216 travels in the distal direction, the pressure surge behind it (enhanced by the flow conditioner 218) continues to accelerate it, thereby increasing the kinetic energy of the micro-particle 216. In addition, the vacuum within the interior volume 203 and the interior channel 207 further enhances the initial pressure differential between the pressurized gas and the evacuated space prior to the abrupt opening of the trigger valve 214, while at the same time reducing drag and/or back-pressure on the micro-particle 216 that might otherwise result from gas swept up in front of the micro-particle 216 as it accelerates distally. As described below, the external cross-sectional size and shape of the micro-particle 216 can be made to be a close fit to the interior cross-sectional size and shape of the interior channel 207, such that the major portion of the pressure surge remains behind the micro-particle 216 without leaking past it.

In accordance with example embodiments, and as discussed below, the micro-particle 216 can exit the open distal end of the interior barrel 206 and pass through the aperture with sufficient momentum (or kinetic energy) to pierce through the membrane 220 and penetrate deeply enough into the dermal tissue to cause a micro-emergence of blood at the surface of the dermal tissue. The residual vacuum within the interior volume 203 of the outer barrel 202, which constitutes negative pressure with respect to air pressure outside the outer barrel 202—and in particular, at the surface of the dermal tissue—can then cause at least a portion of blood from the micro-emergence to be drawn into the interior volume 203.

As described below, the size of the micro-particle 216 can be made sufficiently small, and the kinetic energy developed by the acceleration process made sufficiently large, that the action of puncturing the dermal tissue 222 and causing the micro-emergence of blood can be made imperceptible (or very nearly so) to a person to whom the needle-free blood draw procedure might be applied. More particularly, the small size of the micro-particle 216 can help ensure that the cross-sectional size of the dermal-tissue puncture is smaller than a size that would typically be considered perceptible. At the same time, the very high speed attained by the micro-particle 216 (largely accounting for its high kinetic energy) can help ensure that the action of puncturing the dermal tissue 222 can occur sufficiently suddenly and rapidly to further reduce, or diminish, or eliminate any physical sensation (or perception thereof) that might otherwise result from the action.

In the example operational description above, the gas flow driven by the pressure surge of the released pressurized gas, as well as the micro-particle 216 accelerated by the gas flow, is directed from the proximal to the distal direction. Accordingly, the proximal end of the example hand-portable device 200, and of the components thereof, is also referred to herein as the "upstream" end or side. Similarly, the distal end of the example hand-portable device 200, and of the components thereof, is also referred to herein as the "downstream" end or side. Correspondingly, the proximal direction is also referred to herein as the upstream direction, and the distal direction is also referred to herein as the downstream direction.

Additionally, because evacuation of (i.e., forming a vacuum within) the interior volume 203 of the outer barrel 202 results in negative internal pressure with respect to the ambient pressure outside the outer barrel 202, the outer barrel 202 is also referred to herein as a "negative-pressure barrel." Note that this terminology does not necessarily imply that a vacuum exists within the negative-pressure barrel at all times, but rather that the hand-portable device 200 has at least one operational state (e.g., the armed state) in which a vacuum exists within the negative-pressure barrel. Further, it will be appreciated that the terms "vacuum" and "evacuated" refer to negative internal pressure with respect to the ambient pressure outside the outer barrel 202, and can potentially be used to describe different levels of pressure differential.

As a further note regarding terminology used herein, in view of the use of the inner barrel 206 for accelerating the micro-particle 216, the inner barrel 206 is also referred to herein as an "acceleration barrel." As discussed below, a pressure-drive acceleration barrel, such as the inner barrel 206, can accelerate a micro-particle to nearly supersonic speed, and possibly higher, by the time the micro-particle exits the open distal end of the acceleration barrel. Speeds in this range—namely speeds approaching and/or exceeding supersonic speed—are referred to herein descriptively and "hyperspeeds." Because the acceleration is primarily pressure-driven for the example embodiment shown in FIG. 2, the physical process of accelerating the micro-particle may be described as pneumatic. To signify the high speed attained by the micro-particle, the moniker "hyperspeed particle accelerator" will also be used herein to refer to a hand-portable device for needle-free blood draw, such as the hand-portable device 200 described by way of example above.

In practice, the depth of penetration of the micro-particle, once in exits the aperture 204, can depend on the size of the pressure surge, density of the micro-particle, and the cross-sectional diameter of the micro-particle. More particularly, for a given density and cross-sectional diameter, penetration depth is generally found to increase linearly with pressure. Similarly, for a given pressure and cross-sectional diameter, penetration depth is generally found to increase linearly with density; and for a given density and pressure, penetration depth is generally found to increase linearly with cross-sectional diameter.

In some example embodiments, one or more of the components of a hand-portable device for needle-free blood draw, such as the hand-portable device 200, can be omitted. More specifically, in example embodiments configured for a single application, the chamber volume 212 can be pre-filled with pressurized gas, or the high-pressure gas source 208 can be configured to provide just a single allocation of pressurized gas for filling the chamber volume 212 when the hand-portable device 200 is armed. For such "single-use" embodiments, the metering valve 210 might not serve any purpose, and can therefore be omitted as a component. For "multiple-use" embodiments of the hand-portable device, one purpose of the metering valve 210 might therefore be to provide multiple allocations of pressurized gas for multiple fillings (or re-fillings) the chamber volume 212.

In some example embodiments, the flow conditioner 218 might not be included. For such embodiments, the pressure surge of the released pressurized gas can then just flow directly into the interior channel 207. Alternatively, the proximal end of the interior channel 207 can include a tapered shape that serves as a backstop to the micro-particle 216, preventing it from move proximally from the launch point toward the trigger valve 214. As still a further alternative, the flow conditioner 218, such as a nozzle segment, could incorporate a shape at its distal end that serves as a taper/backstop.

In some example embodiments, the membrane 220 might be omitted. For such embodiments, the dermal tissue might effectively form a membrane to seal the aperture 204 by placement of the aperture directly against the dermal tissue prior to or during evacuation of the interior volume 203 of the negative-pressure barrel. For example, a multiple-use embodiment could use the dermal tissue as a seal of the aperture for each of multiple applications of drawing blood.

Figure 3:
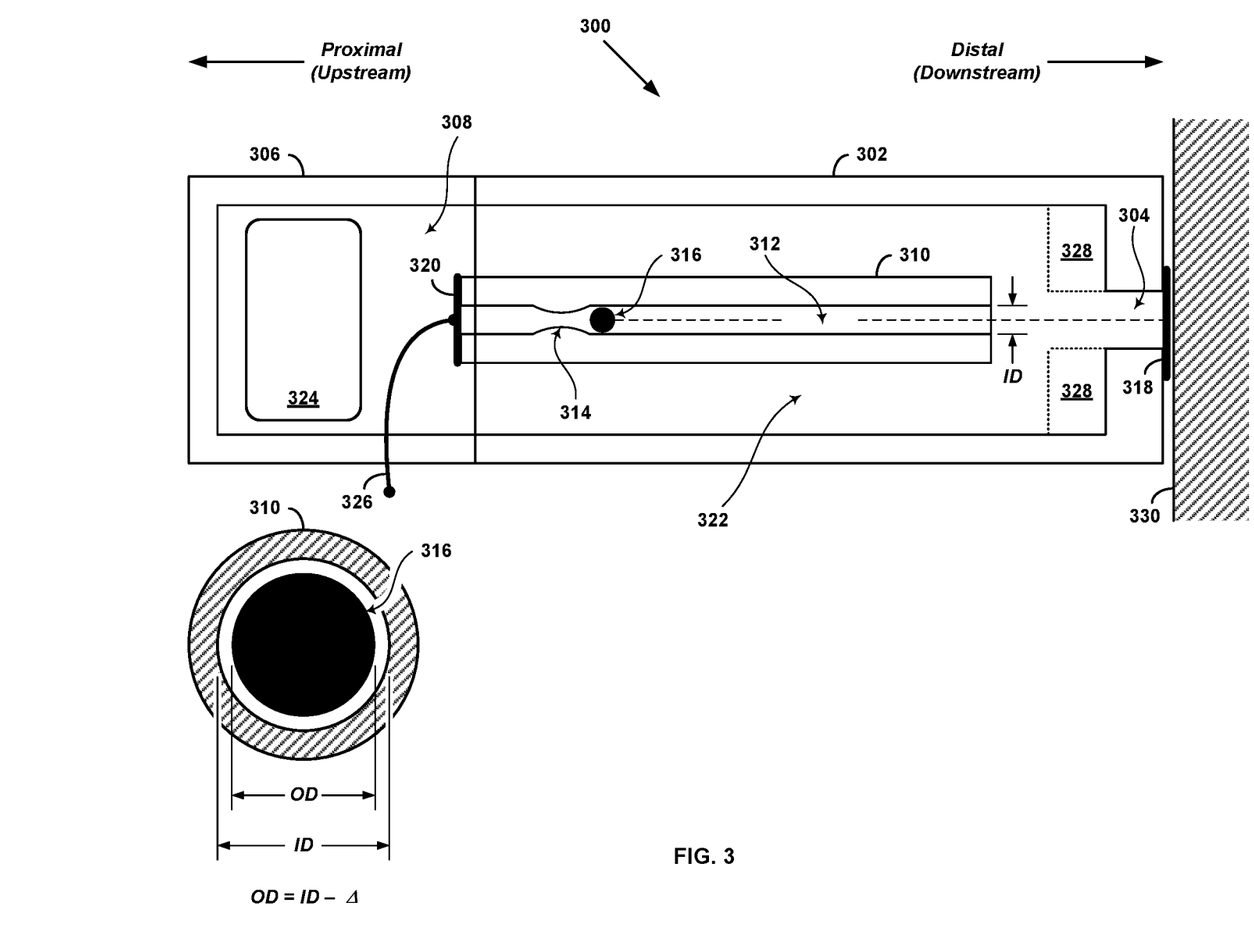
FIG. 3 is an example schematic representation hand-portable device for needle-free blood draw, according to an example embodiment.

Example embodiments of a hand-portable hyperspeed accelerator for needle-free blood draw can be described in further detail by considering FIG. 3, which is an example schematic representation of one form of such a hand-portable device. In FIG. 3, a proximal (and upstream) direction is again depicted to the left, and a distal (and downstream) direction is again depicted to the right. As shown, a hand-portable device 300 can include a negative-pressure barrel 302 with an aperture 304 at its distal end and an interior volume 322 within. In the operational context illustrated, the distal end of the negative-pressure barrel 302 has a membrane 318 that covers and seals the aperture 304. A housing 306 is affixed to the proximal end of the negative-pressure barrel 302. The housing 306 contains a chamber volume 308, which is physically separated from the interior volume 322 of the negative-pressure barrel 302 (although the two volumes 308 and 322 are represented as adjacent to one another in the illustration of FIG. 3, they need not necessarily be so).

In accordance with example embodiments, an accelerator barrel 310 can be positioned longitudinally within, and co-aligned with, the negative-pressure barrel 302. The accelerator barrel 310 has an interior channel 312 running its length with an open distal end and an open, but sealable, proximal end, such that the accelerator barrel 310 can be described as forming a tube. Note that in the operational configuration illustrated in FIG. 3, a trigger valve 320 is depicted as providing a seal covering the open proximal end of the accelerator barrel 310. The open distal end of the accelerator barrel 310 is proximate to, and aligned with, the aperture 304. A horizontal dashed line extending through the interior channel 312 and the aperture 304 in FIG. 3 represents the alignment.

As depicted by way of example in FIG. 3, the distal end of the accelerator barrel 310 appears to extend slightly into the chamber volume 308 of the housing 306. The depth of this extension is not necessarily of significance in the illustration of FIG. 3, but rather is intended to represent that there is a hydrodynamic connection between the chamber volume 308 and the interior channel 312 (and the interior volume 322 by way of the interior channel 312) when the trigger valve 320 is open (e.g., the seal is absent or removed).

The interior channel 312 of the accelerator barrel 310 has an interior cross-sectional shape that is constant over most of its length, except for a short flow-conditioning segment 314 near the proximal end of the interior channel 312. The flow-conditioning segment 314 could be a nozzle segment, for example. By way of example, the interior cross-sectional shape of the interior channel 312 could be a circle with a diameter that then defines an "inner diameter" of the interior channel 312. The inner diameter is indicated by "ID" in FIG. 3.

In accordance with example embodiments, a micro-particle 316 can be positioned initially at a launch point within the interior channel 312, just downstream of the flow-conditioning segment 314, as shown. The micro-particle can have an outer cross-sectional shape in a plane perpendicular to an axis of the acceleration barrel 310 (shown as a horizontal dashed line in FIG. 3) that is substantially similar in form, and only very slightly smaller in size, to the outer cross-sectional shape of the interior channel 312. As such, the micro-particle can travel freely from the launch point to the open distal end of the accelerator barrel 310, with only a minute amount of clearance along the way. In an example configuration, the interior channel 312 can have an inner diameter in a size range of 10 µm to 250 µm and the micro-particle 316 can have an outer diameter in a similar range (where 1 µm=$10^{-6}$ m). As discussed below, the micro-particle 316 can have an outer cross-sectional shape that is not exactly circular or even regular. For example, in some embodiments, the micro-particle 316 can be an agglomeration of nano-sized particles, such that its outer cross-sectional shape has some degree of irregularity. In this sense, the "outer diameter" of the micro-particle 316 can be taken to correspond to the diameter of a circle that circumscribes the outer cross-sectional shape.

The lower left portion of FIG. 3 shows a magnified face-on view of the acceleration barrel 310 and the micro-particle 316. In this view, the outer cross-sectional shape of the micro-particle 316 is represented as circular, with an outer diameter (labeled "OD") that is slightly smaller than the inner diameter (ID) of the acceleration barrel 310 (i.e., the cross-sectional diameter of the interior channel 312). The difference between ID and OD is designated as Δ to signify that the size difference can be small. Note that Δ also corresponds to a clearance between the micro-particle 316 and the circular wall of the interior channel 312 as the micro-particle travels through the interior channel. For purposes of the discussion herein, this close fit between the outer cross-sectional shape and size of the micro-particle 316 and the inner-cross-sectional shape and size of the interior channel 312 is referred to as a "flush fit," with the understanding that there is some degree of clearance (e.g., Δ) along the entire path through the interior channel 310 traveled by the micro-particle 316.

In further accordance with example embodiments, the hand-portable device 300 includes a high-pressure gas source 324, depicted in FIG. 3 as being within the chamber volume 308. In an alternative configuration (not shown), the high-pressure gas source 324 could also be situated outside of the chamber volume 308, but with a means of supplying pressurized gas into the chamber volume 308. The high-pressure gas source 324 can be configured for filling the chamber volume 308 with pressurized gas for driving the pneumatic acceleration of the micro-particle 316. In one example, the high-pressure gas source 324 can be configured for filling the chamber volume 308 just once for a single-use embodiment of the hand-portable device 300. In another example, the high-pressure gas source 324 can be configured for filling the chamber volume 308 multiple times for multiple-use embodiment of the hand-portable device 300. In the case of a multiple-use embodiment, the high-pressure gas source 324 can include a metering valve to control allocations of high-pressure gas (e.g., the metering valve 210 discussed above in connection with FIG. 2).

Also in accordance with example embodiments, the trigger valve 320 can be configured in a closed state and an open state. In its closed state, the trigger valve forms a hydrostatic boundary between the chamber volume 308 and the open proximal end of the accelerator barrel 310. With the trigger valve in its open state, the chamber volume 308 and the open proximal end of the accelerator barrel 310 and the interior channel 312 are hydrodynamically connected. As shown, the trigger valve 320 can also include a release actuator 326 for causing the trigger valve to abruptly transition from its closed state to its open state—i.e., to abruptly open.

By way of example, the trigger valve 320 can be a barrier placed over the distal end of the accelerator barrel 310 to seal the opening. This form of trigger valve is represented by the illustration in FIG. 3. The release actuator 326 can take various forms. In one example, it can be a component configured to deliver an electric voltage and/or current for abruptly rupturing a barrier-based trigger valve. This form of release actuator 326 is suggested by a wire-like element in FIG. 3. In another example, the release actuator 326 can be a mechanical component that mechanically pierces a barrier-based trigger valve. In yet another example, the release actuator 326 can be incorporated as a property of a barrier-based trigger valve that causes the barrier to abruptly rupture when the pressure of the gas in the chamber volume 308 exceeds a threshold. As still another example, the trigger barrier could take the form of a "plug" made of a rapidly-meltable material, such as crystalline wax, and the release actuator 326 could be electrical heater wire or coil. Crystalline wax has a very sharp transition temperature from solid to liquid, such that a plug (trigger barrier) can be rapidly opened by supplying current to the wire or coil. It will be appreciated that other forms of the trigger valve 320 are possible as well.

Operation of the hand-portable device 300 for needle-free blood draw can again be described by way of example. In an operational position in which the hand-portable device is ready (or made ready) for use (e.g., ready to draw blood), the distal end of the outer barrel 302 is placed against (or possibly just very close to) dermal tissue 330. With the trigger valve 320 in the closed state, the chamber volume 308 is filled with pressurized gas from the high-pressure gas source. The interior volume 322 of the negative-pressure barrel 302 can be evacuated to form a vacuum within the interior volume 322 and the interior channel 312 up to the closed trigger valve 320. The closed trigger valve 320 and the membrane 318 sealing the aperture 304 again serve to maintain the vacuum. In this configuration, the hand-portable device 300 armed.

In the armed state, the hand-portable device 300 can be positioned and held with its distal end against the dermal tissue 330, as shown, and with its longitudinal direction approximately perpendicular to the dermal tissue surface. While being held in this position (e.g., manually for a hand-held device or fixedly for a wearable device), the release actuator 326 can be actuated to cause the trigger valve 320 to abruptly open, abruptly releasing a surge of pressurized gas from the chamber volume 308 into the open proximal end of the accelerator barrel 310 by way of the flow-conditioner segment 314. As described above, the pressure surge can accelerate the micro-particle 316 to hyperspeed through the interior channel 312 and the aperture 304. In the process, the micro-particle 316 can acquire sufficient kinetic energy to pierce through the membrane 318 and penetrate the dermal tissue. Again, a resulting micro-emergence of blood from the dermal tissue can be drawn into the negative-pressure barrel 302 by the vacuum within.

In accordance with example embodiment, the launch point within the interior channel is configured very nearly next to the trigger valve 320. That is, the proximal side of flow-conditioner segment 314 can be adjacent to the trigger, and the launch point, where the micro-particle is positioned in the armed state of the device 300 is adjacent to the distal side of the flow-conditioner segment 314. The close proximity of the micro-particle to the source of the pressure surge (i.e., the trigger valve 320) helps insure that the pressure surge delivers an impulse to the micro-particle 316, and helps diminish the possibility of a more gradual pressure build-up behind the micro-particle 316. By way of example, the distance between the trigger valve 320 and the micro-particle 320 at the launch point can be configured to be no larger than the one or two times the diameter of the micro-particle 316.

In further accordance with example embodiments, the interior volume 322 can include a reservoir 328 for collecting and holding the drawn blood. The two regions labeled 328 in FIG. 3 can be taken to represent an annulus viewed from the side. Although not necessarily shown in FIG. 3, the reservoir can include an absorbent material for more efficient collection and storage of the drawn blood. By way of example, the absorbent material can be a hydrophilic absorptive wick (or wicking substance) that can facilitate collection and storage of drawn blood through capillary action. Such a wick could form a partial or total annulus around the opening of the aperture 304, such that is can be close enough to the dermal puncture to make contact with the micro-emergent blood to trigger capillary action, but not obstruct the aperture 304 or the micro-particle's exit path.

In an alternative embodiment, a wicking substance could be have sufficient capillary action to reduce or eliminate the need for vacuum action, reducing or eliminating the role of the vacuum in the interior volume 322 for drawing up the micro-emergence of blood. For such an embodiment, evacuation of the interior volume 322 could be omitted from the hand-portable device 300. The hydrophilic wick could instead function alone in collecting drawn blood.

In accordance with example embodiments, the high-pressure gas source 324 can be a container, such as a cartridge, of pre-pressurized gas that can be released as one or more allocations for filling the chamber volume 308. For example, a cartridge could contain compress atmospheric air, $CO_2$, $N_2$, or He. Other gases could be used as well. It will be appreciated that the lighter gases will flow faster, and vice versa. In an alternative configuration, the high-pressure gas source 324 can be a component configured for generating high-pressure gas. For example, the high-pressure gas source 324 can use a chemical reaction or electrochemical reaction that generates gas pressure. One such mechanism can electrolyze water into hydrogen and oxygen gas within the chamber volume. In still another configuration, the high-pressure gas source 324 can be a component configured for generating high-pressure gas by mechanical means. For example, a plunger or piston could be used to compress gas within a cylinder. The plunger or piston could be actuated by a spring-loaded release lever, for instance. By way of example, the pressure in the filled chamber volume 308 (i.e., filled from the high-pressure gas source 324) could be in a range of 400-1,000 pounds per square inch (psi). Higher pressures, up to and possibly exceeding, 5,000 psi could be used as well.

In further accordance with example embodiments, the membrane 318 used to seal the aperture 304 could be made of a thin foil. Similarly, a thin foil could be used for a barrier-based trigger valve 320. As another example, the membrane and/or the trigger barrier could be made of mylar. As described above, a barrier-based trigger valve could be ruptured mechanically (e.g., by a rupturing implement or by a pressure spike as the chamber volume 308 is filled), or by an electric spark or other electrical process.

In accordance with example embodiments, the interior volume 322 of the negative-pressure barrel can be evacuated in a manufacture process of a single-use embodiment. Alternatively, the hand-portable device 300 could include an evacuation actuator that creates a vacuum in the interior volume 322 prior to a single use of a single-use embodiment, or prior to each of multiple uses of a multiple-use embodiment. For example, an evacuation actuator could be a mechanical plunger or piston that creates a vacuum by being withdrawn from a cylinder. The cylinder could be connected with the interior volume 322 such that it becomes evacuated as the cylinder is withdrawn.

In an alternative multiple-use embodiment, all of the elements distal of the housing 306 could be manufacture as an integrated, single-use (e.g., disposable) component, and the housing 306, the pressurized gas source 324, and the trigger-release 326 could all be integrated as a multiple-use component. In such a "two-component" arrangement, the two components could be made to be easily assembled together (e.g., snap in place) for a given application of a needle-free blood draw (or needle-free sub-dermal delivery of medication, for example). After each use, the disposable component could be removed and delivered to a blood analysis lab or local apparatus that could fully analyze the blood, or partially analyze it and upload the partially-analyzed results to a network-based analysis facility for complete analysis. Alternatively, the multiple-use component could include an integrated analysis test module that could perform the test in place. Such an arrangement could be made part of a wearable device, for example. The disposable component could then be removed and discarded, and a new (unused) disposable component installed.

In further accordance with the two-component configuration, the disposable components could be manufactured to as sterile components, and packaged sterilely. Assembly of the two components could use a procedure that maintains the sterility of the disposable component so that it remains sterile through use and analysis of the blood sample (or delivery of the medication or therapeutic monitoring substance).

In accordance with example embodiments, both the single-use and multiple-used configurations can include a means for sterilizing the dermal tissue prior to application of the device. By way of example, the distal end of the negative-pressure barrel could include an alcohol (or other sterilizing substance) dispenser that flushes the dermal tissue over an area that will include the puncture point. Alternatively, sterilization could be achieved with a pulse of ultra-violet (UV) radiation, or a heat pulse. In still further accordance with example embodiments, an anti-coagulant, such as heparin, could be applied prior to a blood draw in order to help ensure that the micro-emergence of blood does not clot before being drawn up into the reservoir 328. The anti-coagulant could be applied by an integrated dispenser, for example.

Figure 4:
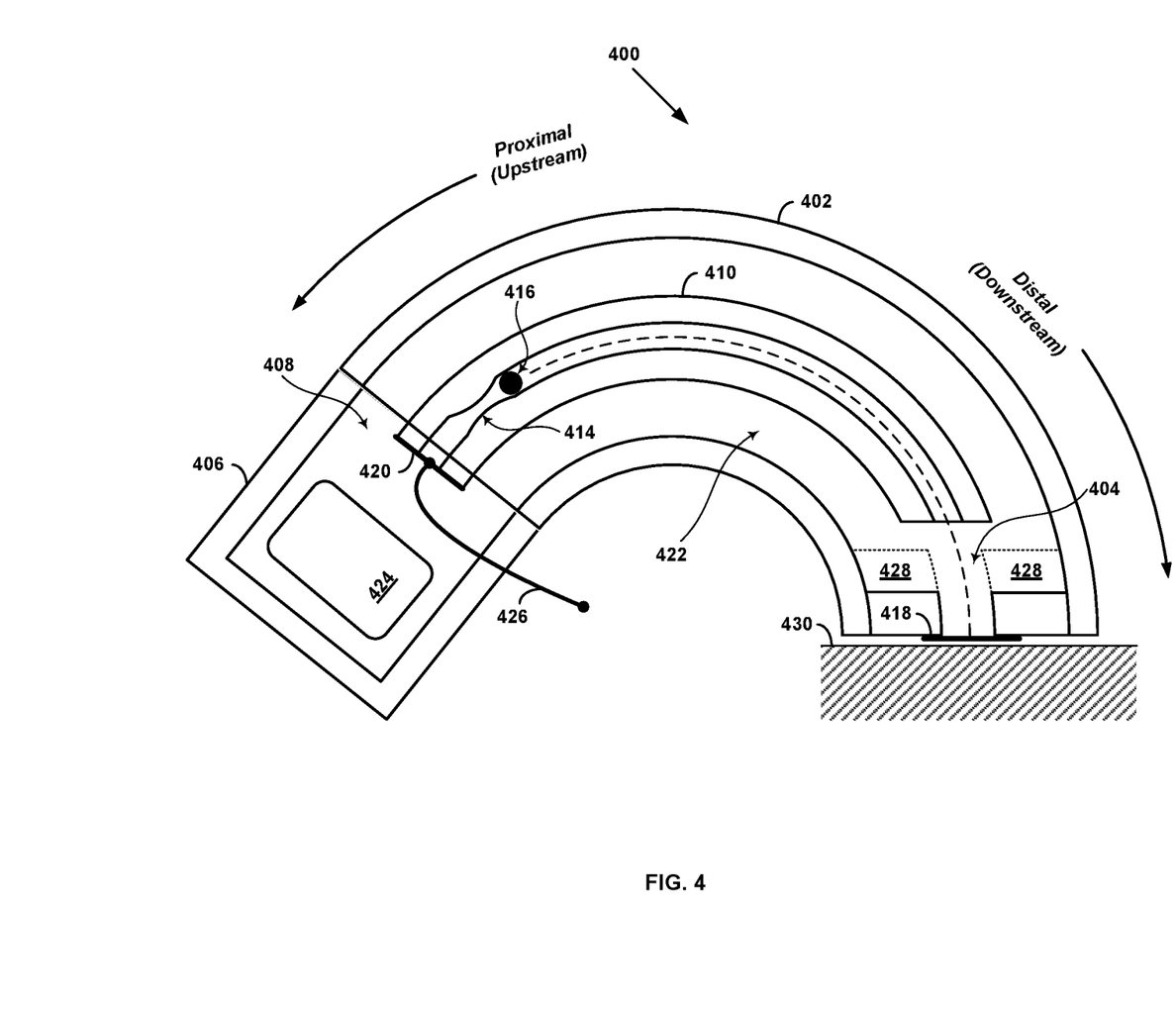
FIG. 4 is an example schematic representation hand-portable device for needle-free blood draw, according to an alternative example embodiment.

FIG. 4 is an example schematic representation of an alternative embodiment of a hand-portable device 400 for needle-free blood draw, according to an alternative example embodiment. Specifically, the hand-portable device 400 includes most or all of the elements of the hand-portable device 300 discussed above, but, as shown, the barrel elements of the hand-portable device 400 are curved. A curve configuration can be used, for example, to accommodate a more compact form factor than might be accommodated by a straight configuration such as the one shown in FIG. 3. A compact configuration could be beneficial for a wearable embodiment, such the wristband example illustrated in FIG. 1B.

The specific elements of the hand-portable device 400 include a curved negative pressure barrel 402, with an aperture 404 at its distal end and an interior volume 422 within. The distal end of the negative-pressure barrel 402 has a membrane 418 that covers and seals the aperture 404. A housing 406 is affixed to the proximal end of the negative-pressure barrel 402. The housing 406 contains a chamber volume 408, which is physically separated from the interior volume 422 of the negative-pressure barrel 402. A high-pressure gas source 424 is configured within the chamber volume 408. In the illustration of FIG. 4, the sealed aperture 404 is depicted as adjacent to dermal tissue 430.

A curved accelerator barrel 410 is positioned co-linearly with the negative-pressure barrel 402. The accelerator barrel 410 has a curved interior channel 412 running its length with an open distal end and an open, but sealable, proximal end. The open distal end of the accelerator barrel 410 is proximate to, and aligned with, the aperture 404. A curved dashed line extending through the interior channel 412 and the aperture 404 in FIG. 4 represents the alignment. The interior channel 412 has an interior cross-sectional shape that is constant over most of its length, except for a short flow-conditioning segment 414 near the proximal end of the interior channel 412. The flow-conditioning segment 414 could be a nozzle segment, for example. In the operational configuration illustrated in FIG. 4, a trigger valve 420 is depicted as providing a seal covering the open proximal end of the accelerator barrel 410. As shown, the trigger valve 420 can also include a release actuator 426 for causing the trigger valve to abruptly transition from its closed state to its open state—i.e., to abruptly open.

A micro-particle 416 can be positioned initially at a launch point within the interior channel 412, just downstream of the flow-conditioning segment 414, as shown. The micro-particle can have an outer cross-sectional shape in a plane perpendicular to an axis of the acceleration barrel 410 that is substantially similar in form, and only very slightly smaller in size, to the outer cross-sectional shape of the interior channel 412.

Operation of the hand-portable device 400 for needle-free blood draw is largely same as that described above for the hand-portable device 300, and is not described further.

Note that, as with the illustration of the hand-portable device 200 in FIG. 2, the neither the sizes of the components, nor their relatives sizes, of the hand-portable devices 300 and 400 in FIGS. 3 and 4 are necessarily shown to scale.

3. Illustrative Micro-Particles

In accordance with example embodiments, the micro-particle can have a spherical, ellipsoidal, or cylindrical shape, and a characteristic size (e.g., diameter) in range of 10 μm (microns)-250 μm. The micro-particle can be metallic (e.g., iron) or biodegradable (e.g., salt, sugar, or polylactic-co-glycolic acid (PLGA)). The micro-particle can also be composed of multiple, smaller particles, or an agglomerate of smaller particles. For example, the micro-particle could be made of nano-sized gold particles bound together with biodegradable glue. In general, the higher the density of the micro-particle, the deeper the penetration of the dermal tissue. Other forms and compositions of micro-particles are possible as well. For example, the micro-particle could be a small droplet liquid, such as water. Further, the micro-particle could be positioned at the launch point with a small amount of liquid (e.g., water) just behind it (i.e., on the proximal—up stream—side of the particle). This configuration could be used to effectively increase the mass of the micro-particle, thereby boosting the total acquired momentum and resulting dermal penetration depth.

In further accordance with example embodiments, the micro-particle can provide therapeutic value beyond just inducing a micro-emergence of blood for a needle-free blood draw. For example, a micro-particle could carry medication for delivery into a patient. Additionally or alternatively, a micro-particle could have physical properties that make it suitable for diagnostic monitoring of a patient.

4. Example Method

Figure 5:
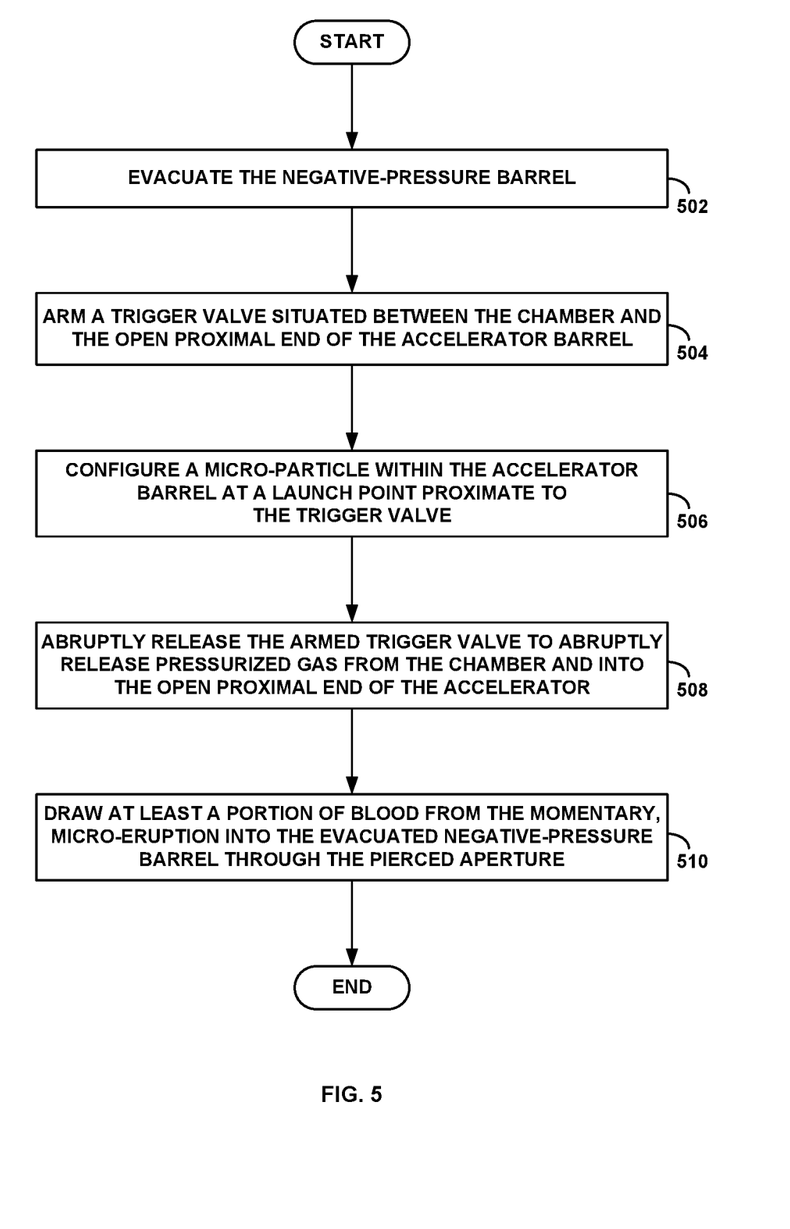
FIG. 5 is a flowchart of an example method of needle-free blood draw using a hand-portable device for needle-free blood draw, according to an example embodiment.

FIG. 5 is a flowchart illustrating an example method of needle-free blood draw using a hand-portable hyperspeed particle accelerator, according to an example embodiment. The example method could be carried out using a hand-portable hyperspeed particle accelerator such as the hand-portable device 300 or 400 discussed above.

At step 502, a negative-pressure barrel of a hand-portable hyperspeed particle accelerator is evacuated.

At step 504, a trigger valve situated between a chamber volume and an open proximal end of an acceleration barrel is armed, or closed. Arming or closing the trigger valve creates a hydrostatic boundary between the chamber volume and the interior channel of the acceleration barrel.

At step 506, a micro-particle is configured a launch point within the acceleration barrel, proximate to the trigger valve. As described above, the launch point is downstream of the trigger valve, but near the proximal end of the accelerator barrel.

At step 508, the armed trigger valve is abruptly open to abruptly release pressurized gas from the chamber volume into the open proximal end of the accelerator barrel. As described above, the resulting surge of gas can accelerate the micro-particle to hyperspeed, approaching or exceeding the speed of sound. The micro-particle can thereby attain enough kinetic energy to pierce through a membrane, such as a thin foil, covering an aperture at the distal end of the negative-pressure barrel, and penetrate dermal tissue proximate to the aperture. Penetration of the dermal tissue can then result in a micro-emergence of blood at the surface of the dermal tissue.

At step 510, at least a portion of blood from the micro-emergence of blood is drawn into the negative-pressure barrel through the aperture.

In further accordance with example embodiments, the hand-portable hyperspeed particle accelerator can be configured for multiple applications by repeating the steps 502-510. Specifically, the negative-pressure barrel can be re-evacuated, the trigger valve can be re-armed, and a replacement micro-particle can be re-configured at the launch point. A subsequent application of needle-free blood drawing can then be accomplished by re-releasing the re-armed trigger valve, and again drawing at least a portion of blood from a subsequent micro-emergence of blood at the dermal tissue surface.

It will be appreciated that the steps shown in FIG. 5 are meant to illustrate a method in accordance with example embodiments. As such, various steps could be altered or modified, the ordering of certain steps could be changed, and additional steps could be added, while still achieving the overall desired operation.

The method illustrated in FIG. 5 can be viewed more generally as a method for creating a pore-size skin puncture by accelerating a micro-particle at a dermal tissue surface using a hand-portable hyperspeed micro-particle accelerator. The generalized steps of the method include configuring a micro-particle at a launch point at a proximal end of an accelerator barrel of a hand-portable hyperspeed micro-particle accelerator device. The accelerator barrel can be positioned lengthwise within an outer barrel of the hand-portable hyperspeed micro-particle accelerator device and can have an open distal end proximate to, and aligned with, an aperture at a distal end of the outer barrel. The hand-portable hyperspeed micro-particle accelerator device can be armed, such that it is placed in a ready state for accelerating the micro-particle. In the armed state, the hand-portable hyperspeed micro-particle accelerator device can then be triggered, thereby causing the micro-particle to accelerate from the launch point to the open distal end of the accelerator barrel and through the aperture with sufficient momentum to pierce dermal tissue and creating a surface puncture no larger than a dermal pore in size.

While the hand-portable hyperspeed micro-particle accelerator device has been described by way of example embodiment as a pneumatic accelerator, other embodiments of micro-particle accelerator mechanism are possible. For example, hyperspeed acceleration of a micro-particle could be achieve with an electromagnetic railgun, for example. Such an alternative embodiment could also be used for needle-free blood draw (or sub-dermal delivery of medicine or therapeutic monitoring substances) in manner similar to the methods discussed above.

5. Conclusion

While various aspects and embodiments have been disclosed herein, other aspects and embodiments will be apparent to those skilled in the art. The various aspects and embodiments disclosed herein are for purposes of illustration and are not intended to be limiting, with the true scope being indicated by the following claims.

What is claimed is:

1. A hand-portable device comprising:
    a negative-pressure barrel having an aperture opening at a distal end and a housing affixed to a proximal end;
    an accelerator barrel positioned lengthwise within the negative-pressure barrel with an open proximal end fixed to the housing and opening into a chamber within the housing, and having an open distal end proximate to, and aligned with, the aperture;
    a high-pressure gas source configured for filling the chamber with pressurized gas; and
    a trigger valve situated between the chamber and the open proximal end of the accelerator barrel, the trigger valve having a closed operational state in which the trigger valve is closed so as to form a hydrostatic boundary between the chamber and the open proximal end of the accelerator barrel, and an open operational state in which the trigger valve is opened so as to remove the hydrostatic boundary,
    wherein the hand-portable device has an armed operational state in which (i) the trigger valve is set in the closed operational state, (ii) the chamber is filled with pressurized gas, (iii) a micro-particle is positioned within the accelerator barrel at a launch point proximate to the trigger valve, (iv) a negative-pressure vacuum is created within the negative-pressure barrel and within the accelerator barrel between the open distal end and the closed trigger valve, and (v) an aperture membrane is configured to seal the aperture and maintain the negative-pressure vacuum,
    wherein the hand-portable device further comprises:
    a trigger-valve release actuator configured for causing the trigger valve to abruptly transition from the closed operational state to the open operational state, thereby abruptly releasing the pressurized gas from the chamber into the open proximal end of the accelerator barrel,
    wherein, the pressure of the pressurized gas is configured to be sufficient for abrupt release into the open proximal end of the accelerator barrel to accelerate the micro-particle from the launch point to the open distal end of the accelerator barrel and through the aperture with sufficient momentum to pierce through the aperture membrane and, when the distal end of the negative-pressure barrel is positioned proximate to dermal tissue, to penetrate a sufficient depth of the dermal tissue to cause a micro-emergence of blood at the dermal tissue surface, and wherein, when the distal end of the negative-pressure barrel is positioned proximate to the dermal tissue, the negative-pressure vacuum within the negative-pressure barrel is sufficient to cause at least a portion of blood from the micro-emergence to be drawn into the negative-pressure barrel through the pierced aperture membrane, and the hand-portable device further comprises a reservoir at the distal end of the negative-pressure barrel configured for collecting and holding the at least a portion of blood drawn.

2. The hand-portable device of claim 1, wherein the high-pressure gas source is selected from a list consisting of a container of compressed gas, a chemically-reactive gas pressure generator apparatus, an electro-chemical gas pressure generator apparatus, and a mechanical pressure generator.

3. The hand-portable device of claim 1, wherein the accelerator barrel comprises an inner cylindrical channel having a constant interior cross-sectional shape between the launch point and the open distal end, and wherein the micro-particle has an exterior cross-sectional shape configured to be a flush fit to the constant interior cross-sectional shape of channel and at the same time not impede free longitudinal motion of the micro-particle through the channel.

4. The hand-portable device of claim 3, wherein the interior cross-sectional shape of the inner cylindrical channel is circular and the exterior cross-sectional shape of the micro-particle is substantially circular.

5. The hand-portable device of claim 3, wherein the inner cylindrical channel comprises a nozzle segment situated between the launch point and the trigger valve, the nozzle segment being configured to cause the abruptly released pressurized gas entering from the chamber to exit the nozzle segment toward the micro-particle as a supersonic flow.

6. The hand-portable device of claim 3, wherein the inner cylindrical channel comprises a taper segment situated between the launch point and the trigger valve, the taper segment forming a backstop configured to prevent motion of the micro-particle from the launch point toward the trigger valve.

7. The hand-portable device of claim 3, wherein the trigger valve comprises a trigger barrier configured to form a hydrostatic seal between the chamber and the open proximal end of the accelerator barrel when the trigger valve is set in the closed operational state, and wherein the trigger-valve release actuator comprises a rupture actuator configured for abruptly rupturing the trigger barrier to abruptly break the hydrostatic seal.

8. The hand-portable device of claim 1, further comprising a metering valve configured for controlling separate refill allocations of pressurized gas from the high-pressure gas source to fill the chamber.

9. The hand-portable device of claim 1, wherein, when the distal end of the negative-pressure barrel is positioned proximate to the dermal tissue, the dermal tissue surface serves as the aperture membrane by placement of the aperture in direct contact against the dermal tissue surface.

10. A method comprising:

evacuating a negative-pressure barrel of a hand-portable device, the evacuated negative-pressure barrel having an aperture membrane sealing an aperture at a distal end of the negative-pressure barrel, and a housing affixed to, and sealing, a proximal end of the negative-pressure barrel, wherein the negative-pressure barrel contains an accelerator barrel positioned lengthwise within the negative-pressure barrel with an open proximal end fixed to the housing and opening into a chamber within the housing, and having an open distal end proximate to, and aligned with, the aperture;

arming a trigger valve situated between the chamber and the open proximal end of the accelerator barrel, the armed trigger valve forming a hydrostatic boundary between chamber and the open proximal end of the accelerator barrel;

configuring a micro-particle within the accelerator barrel at a launch point proximate to the trigger valve;

positioning the distal end of the negative-pressure barrel proximate to dermal tissue;

by abruptly releasing the armed trigger valve, abruptly releasing pressurized gas from the chamber and into the open proximal end of the accelerator, wherein the pressure of the pressurized gas is configured to be sufficient for abrupt release into the open proximal end of the accelerator barrel to accelerate the micro-particle from the launch point to the open distal end of the accelerator barrel and through the aperture with sufficient momentum to pierce through the aperture membrane and, when the distal end of the negative-pressure barrel is positioned proximate to the dermal tissue, to penetrate a sufficient depth of the dermal tissue to cause a micro-emergence of blood at the dermal tissue surface; and drawing at least a portion of blood from the micro-emergence into a reservoir at the distal end of the negative-pressure barrel configured for collecting and holding the at least a portion of drawn blood.

11. The method of claim 10, further comprising, subsequent to drawing the at least a portion of blood:

re-evacuating the negative-pressure barrel of a hand-portable device;

re-arming the trigger valve;

re-configuring a replacement micro-particle within the accelerator barrel at the launch point;

abruptly re-releasing the re-armed trigger valve; and drawing at least a portion of blood from a subsequent micro-emergence at the dermal tissue surface.

12. The method of claim 10, further comprising piercing, with the accelerated micro-particle, the dermal tissue proximate to the distal end of the outer barrel with no larger than a dermal-pore-sized surface puncture.

* * * * *